United States Patent [19]
Bacher et al.

[11] Patent Number: 5,650,509
[45] Date of Patent: Jul. 22, 1997

[54] STERICALLY HINDERED PHENOLS

[75] Inventors: Jean-Pierre Bacher, Buschwiller, France; Manfred Rembold, Aesch, Switzerland; Dieter Reinehr, Kandern, Germany

[73] Assignee: Ciba-Geigy Corporation, Tarrytown, N.Y.

[21] Appl. No.: 541,005

[22] Filed: Oct. 11, 1995

Related U.S. Application Data

[62] Division of Ser. No. 229,036, Apr. 18, 1994, abandoned.

[30] Foreign Application Priority Data

Apr. 22, 1993 [CH] Switzerland .............. 1228/93

[51] Int. Cl.$^6$ .............................. C07D 251/22
[52] U.S. Cl. .......................... 544/193.1; 562/51
[58] Field of Search ............. 562/51; 544/193.1

[56] References Cited

U.S. PATENT DOCUMENTS

| | | |
|---|---|---|
| 2,527,425 | 10/1950 | Keller et al. . |
| 3,665,031 | 5/1972 | Peterli et al. . |
| 5,096,456 | 3/1992 | Reinert . |
| 5,181,935 | 1/1993 | Reinert . |

FOREIGN PATENT DOCUMENTS

| | | |
|---|---|---|
| 0438381 | 7/1991 | European Pat. Off. . |
| 0459950 | 12/1991 | European Pat. Off. . |
| 0475907 | 3/1992 | European Pat. Off. . |

OTHER PUBLICATIONS

Chem. Abstract, vol. 76, #12, #60909g, (1972), Yamashita.

*Primary Examiner*—Nicky Chan
*Attorney, Agent, or Firm*—Kevin T. Mansfield

[57] ABSTRACT

Sterically hindered phenols of formula (1) are disclosed. These antioxidants are suitable for enhancing the thermal and photochemical stability of undyed and dyed polyamide fibre materials. They are distinguished by superior exhaustion which is almost independent of the pH.

6 Claims, No Drawings

STERICALLY HINDERED PHENOLS

This is a division of Ser. No. 08/229,036, filed Apr. 18, 1994, now abandoned.

The present invention relates to water-soluble sterically hindered phenols, to a process for the preparation of these compounds, to a process for the photochemical and thermal stabilisation of polyamide fibre materials using said compounds and to the fibre material treated therewith.

The water-soluble sterically hindered phenols have the formula

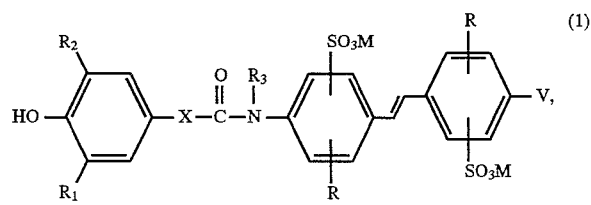

wherein

R is hydrogen, halogen, lower alkyl or lower alkoxy, $R_1$ and $R_2$ are each independently of the other hydrogen, methyl or tert-butyl, and the sum of the carbon atoms of $R_1$ and $R_2$ is at least 2, $R_3$ is hydrogen or an unsubstituted or substituted alkyl group, X is alkylene, oxaalkylene or thiaalkylene, V is a radical of formula

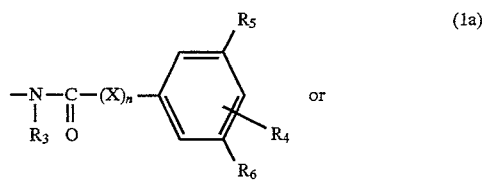

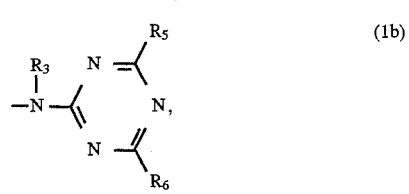

$R_4$ is hydrogen, halogen, lower alkyl or lower alkoxy, $R_5$ and $R_6$ are each independently of the other hydrogen, halogen, lower alkyl, lower alkoxy, amino, mono-lower alkylamino, di-lower alkylamino, phenoxy, phenylamino or phenyl-lower alkylamino, M is hydrogen, alkali metal, alkaline earth metal, ammonium or an organic ammonium radical, and n is 0 or 1.

In the definition of the substituents R, $R_4$, $R_5$ and $R_6$ lower alkyl, lower alkoxy, mono-lower alkylamino and di-lower alkylamino denote those groups or moieties that contain 1 to 5, preferably 1 to 3, carbon atoms. Typical examples of such groups are methyl, ethyl, n-propyl, isopropyl, n-butyl, sec-butyl, tert-butyl, amyl or isoamyl and, respectively, methoxy, ethoxy, isopropoxy, isobutoxy, tert-butoxy or tert-amyloxy.

Phenyl-lower alkylamino is typically phenethylamino, phenylpropylamino, phenylbutylamino or, preferably, benzylamino.

Mono-lower alkylamino and di-lower alkylamino may be substituted by halogen, lower alkoxy, hydroxy, carboxy or carboxy-lower alkyl. Lower alkoxy may be substituted by lower alkoxy. Phenyl may be substituted by lower alkyl, lower alkoxy or halogen.

$R_3$ as straight-chain or branched alkyl can contain 1 to 18, preferably from 1 to 8, carbon atoms. Illustrative examples of such groups are methyl, ethyl, isopropyl, pentyl, octyl, dodecyl and octadecyl.

$R_3$ as a substituted alkyl group may be a hydroxyalkyl, alkoxyalkyl, aminoalkyl, alkylaminoalkyl or dialkylaminoalkyl group containing a total of 2 to 10, preferably of 2 to 5, carbon atoms. Illustrative examples of such groups are β-hydroxyethyl, β-methoxyethyl, β-aminoethyl, β, β-diethylaminoethyl or β-butylaminoethyl.

Halogen substituents R, $R_4$, $R_5$ and $R_6$ are fluoro, bromo or, preferably, chloro.

X can be straight-chain or branched and can contain 1 to 8, preferably 1 to 5, carbon atoms. Illustrative examples of such groups are methylene, ethylene, trimethylene, propylene, 2-thiatrimethylene or 2-oxapentamethlene.

Exemplary alkali metals are lithium, sodium or potassium. Exemplary alkaline earth metals are calcium and magnesium. Owing to the sparing solubility of certain calcium, strontium and barium salts in aqueous media and for economic reasons, preferred compounds of formula (1) are those obtained in the form of their sodium, lithium, magnesium or ammonium salts or of the ammonium salt of an organic nitrogen base. Illustrative examples of such nitrogen bases that are able to form ammonium salts with the $SO_3$ group are trimethylamine, triethylamine, triethanolamine, diethanolamine, ethanolamine, cyclohexylamine, dicyclohexylamine, hexamethyleneimine or morpholine.

Sterically hindered phenols having an interesting utility are those compounds of formula (1) in which V is a radical of formula (1b) or

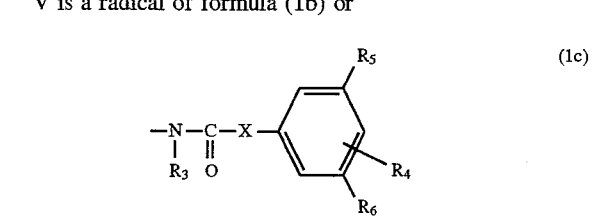

and $R_3$, $R_4$, $R_5$ and X are as defined for formula (1a).

Particularly preferred compounds are those in which $R_3$ is hydrogen or straight-chain or branched $C_1$-$C_8$alkyl, and, most particularly, those compounds in which $R_3$ is hydrogen.

Among the compounds of formula (1), those compounds are preferred in which $R_1$ and $R_2$ are each independently of the other methyl or tert-butyl and, most particularly, those compounds in which $R_1$=$R_2$=tert-butyl.

Compounds of particular interest are those of formula (2)

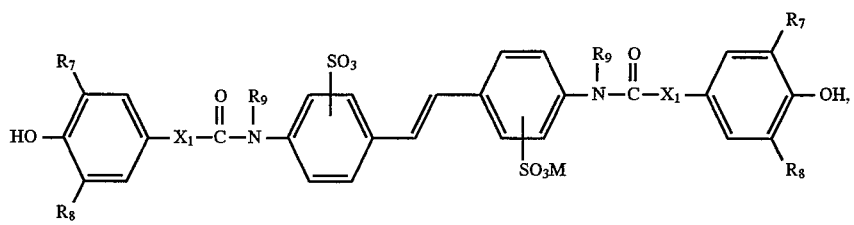

wherein
- $R_7$ and $R_8$ are each independently of the other methyl or tert-butyl,
- $R_9$ is hydrogen or lower alkyl,
- $X_1$ lower alkylene, and
- M is hydrogen or sodium.

The water-soluble sterically hindered phenols of formulae (1) and (2) are novel compounds. They can be prepared by methods that are known per se, typically as described in U.S. Pat. No. 3,665,031. They are prepared by reacting 1 mol of the compound of formula

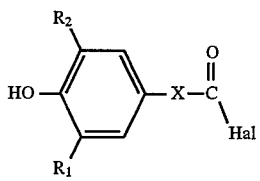

with 1 mol of the compound of formula

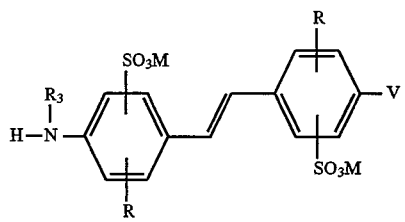

wherein
- Hal is halogen, and
- R, $R_1$, $R_2$, $R_3$, V, X and M have the given meanings.

The water-soluble sterically hindered phenols are suitable for the photochemical and thermal stabilisation of dyed and undyed polyamide fibre materials.

In U.S. Pat. No. 3,665,031 it is taught to protect undyed polymers, e.g. polyamides, against the action of heat and/or oxygen (atmospheric oxidation) using water-soluble phenolic antioxidants.

U.S. Pat. No. 5,096,456 discloses a process for enhancing the thermal and/or photochemical stability of dyeings on polyamide fibres by treating the dyed polyamide fibres with phenolic water-soluble antioxidants.

Compared with the antioxidants described in these references, the selected compounds of this invention are distinguished by superior exhaustion that is essentially independent of the pH. The compounds of the invention are therefore especially suitable for use in dyebaths which contain metal complex dyes and have a pH of 7 to 7.5.

The process for the photochemical stabilisation of polyamide fibre materials using the novel sterically hindered phenols therefore constitutes a further object of the invention.

The process comprises treating dyed or undyed fibre material with a sterically hindered phenol of formula

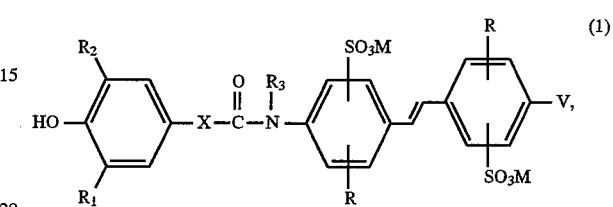

wherein
- R is hydrogen, halogen, lower alkyl or lower alkoxy,
- $R_1$ and $R_2$ are each independently of the other hydrogen, methyl, tert-butyl and the sum of the carbon atoms of $R_1$ and $R_2$ is at least 2,
- $R_3$ is hydrogen or an unsubstituted or substituted alkyl group,
- X is alkylene, oxaalkylene or thiaalkylene,
- V is a radical of formula

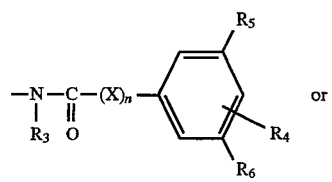

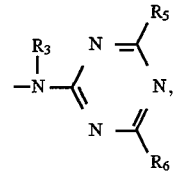

- $R_4$ is hydrogen, halogen, lower alkyl or lower alkoxy,
- $R_5$ and $R_6$ are each independently of the other hydrogen, halogen, lower alkyl, lower alkoxy, amino, mono-lower alkylamino, di-lower alkylamino, phenoxy, phenylamino or phenyl-lower alkylamino,
- M is hydrogen, alkali metal, alkaline earth metal, ammonium or an organic ammonium radical, and
- n is 0 or 1.

The compounds of formula (1) can be applied to the polyamide fibre materials from customary liquors by standard methods. In the process of this invention they are applied from an aqueous bath that contains the compounds in an amount of 0.005 to 10% by weight, preferably 0.05 to 2% by weight. It is preferred to carry out the treatment with the novel compounds and dyeing in the same application bath. The procedure can conveniently comprise first adding the antioxidant to the aqueous application bath, treating the appropriate fibre material and then dyeing the treated material, or adding the antioxidant and the dye to the bath simultaneously, or first dyeing the material and then effecting the treatment with the antioxidant. The simultaneous application of antioxidant and dyeing is preferred. Application can be made by an exhaust or continuous process.

In the exhaust process, the liquor ratio can be chosen over a wide range, conveniently from 1:5 to 1:300, preferably from 1:10 to 1:50. The process is conveniently carried out in the temperature range from 30° to 120° C., preferably from 50° to 98° C.

In the continuous process, the liquor pick-up is preferably 30–400% by weight, preferably 75–250% by weight. To fix the dyes and the compounds of formula (1), the fibre material is subjected to a heat treatment. Fixing can also be effected by the cold pad-batch method.

The heat treatment is preferably carried out by steaming in a steamer with steam or superheated steam in the temperature range from 98° to 105° C. for conveniently 1 to 7, preferably 1 to 5, minutes. The fixation of the dyes and the compounds of formula (1) by the cold pad-batch method can be effected by storing the impregnated and preferably rolled up goods at room temperature (15°–30° C.), conveniently for 3 to 24 hours, the cold batching time depending naturally on the type of dye used.

When the dyeing process and fixation are complete, the dyeings are washed off and dried in conventional manner.

The polyamide fibre materials obtained, and the dyeings produced thereon, by the process of this invention have good photochemical and thermal stability.

The dyeings that are photochemiocally and thermally stabilised in the practice of this invention are those produced with acid or metal complex dyes, typically 1:2 chromium, 1:2 cobalt or copper complex dyes, or with disperse and reactive dyes.

Examples of such dyes are listed in the Colour Index, 3rd Edition 1971, Volume 4.

Polyamide fibre material will be understood as meaning in the context of this invention synthetic polyamide, including polyamide 6, polyamide 66 or polyamide 12, as well as modified polyamide, e.g. basic dyeable polyamide. In addition to pure polyamide fibres, polyurethane and polyamide blends, for example tricot material made from poly-amide/polyurethane in the ratio 70:30 are also suitable. Basically, the pure polyamide material or blends thereof may be in any form of presentation, including fibres, yarn, woven fabrics, knitted fabrics, nonwovens or pile material.

The process of this invention is especially suitable for treating polyamide fibre material that is exposed to the influence of light and heat, for example car upholstery or carpets.

The invention is illustrated by the following Examples in which parts and percentages are by weight.

EXAMPLE 1

18.4 g of 4,4'-diaminostilbene-2,2'-disulfonic acid and 37 g of tributylamine are together dissolved in 400 ml of dimethyl formamide at 70° C. The solution is cooled to 50° C., then 81 g of a solution of β-(4-hydroxy-3,5-di-tert-butylphenyl)propionyl chloride (55%) are added and the mixture is stirred for 24 hours at 50° C. The reaction solution is concentrated by evaporation under a water jet vacuum and the residue is stirred in 500 ml of ethyl acetate and isolated by filtration. The filter product is washed with a further 500 ml of ethyl acetate to give 44 g of a pale beige product of formula

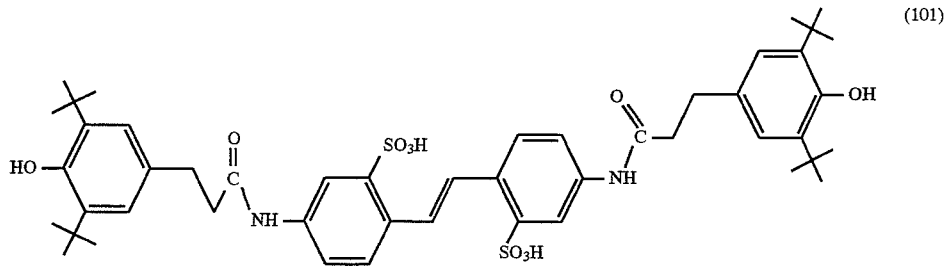

Yield: 94% of theory
$\lambda_{max}$=337 nm

EXAMPLE 2

The compound of formula (102)

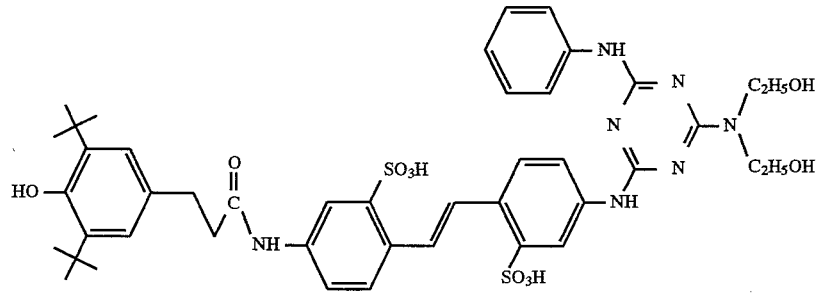

is obtained in similar yield by replacing 4,4'-diaminostilbene-2,2'-disulfonic acid with the following aminostilbene of formula

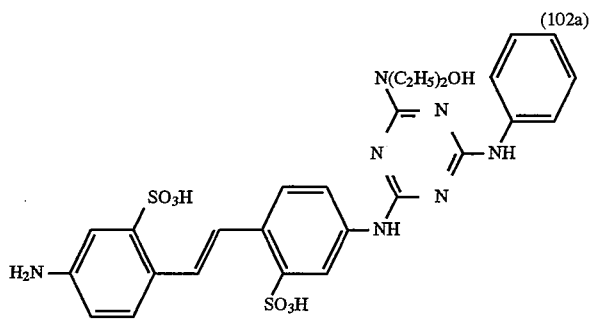

The compound of formula (102a) is prepared by reaction of 4-amino-4'-nitro-2,2'-disulfonic acid with cyanuric chloride, subsequent reaction with aniline and diethylamine and final Bechamp reduction of the nitro group to an amino group.

EXAMPLES 3 to 6

The following compounds can be prepared in accordance with the general procedure described in Example 2:

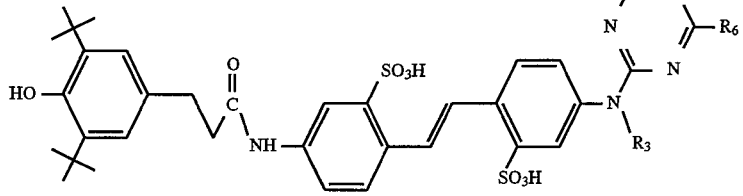

Application Example

EXAMPLE 2

2 samples (10 g each) of polyamide 6 knitwear (Lilion texturised tricot 5-4003) are dyed in a dyeing machine, e.g. Vistacolor (supplied by Zeller), at a liquor to goods ratio of 1:25. The 2 baths contain the following additional ingredients:

1 g/f of sodium phosphate in the ratio of 25 parts of monosodium salt to 175 parts of disodium salt (pH 7.5), as well as 1% of a nonionic levelling agent, based on the textile material.

Whereas liquor 1 contains no further ingredients, 1% of the compound of formula (101), based on the textile material, is added to THE liquors 2.

The fabric is put at 45° C. into the so prepared liquors, which are heated to 95° C. over 45 minutes. After a dyeing time of 40 minutes at 95° C., the liquors are cooled to 60° C. and the fabric is rinsed with cold water, centrifuged and dried at room temperature.

The treated samples are irradiated in accordance with DIN 75.202 (FAKRA) and the tear strength is determined according to SN 198,461. The results are reported in Table 2:

TABLE 2

| Addition to dyebath | Tear strength after 120 h FAKRA irradiation in % |
|---|---|
| none | 10 |
| 1% of compound (101) | 31 |

Two further samples are subjected to a heat test. The samples are aged for 72 hours in a circulating air oven at 140° C. and the tear strength according to SN 198,461 is determined. The results are reported in Table 3.

TABLE 3

| Addition to dyebath | Tear strength after 72 h at 140° C. in % |
|---|---|
| none | 10 |
| 1% of compound (101) exhaustion 94% | 91 |

The tear strength of the knitted fabric treated with the novel compound is markedly higher upon exposure to photochemical and thermal stress.

TABLE 1

| Compound No. | $R_3$ | $R_5$ | $R_6$ |
|---|---|---|---|
| (103) | H | —NH—C₆H₅ | morpholino |
| (104) | H | —NH—C₆H₄—SO₃Na | —N(C₂H₅OH)₂ |
| (105) | H | —NH—C₆H₄—SO₃Na | —N(C₂H₅OH)₂ |
| (106) | H | —NH—C₆H₃(SO₃Na)₂ | morpholino |

What is claimed is:

1. A sterically hindered phenol of the formula

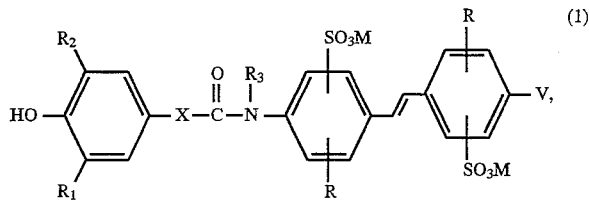

wherein

R is hydrogen, halogen, lower alkyl or lower alkoxy, $R_1$ and $R_2$ are each independently of the other hydrogen, methyl or tert-butyl and the sum of the carbon atoms of $R_1$ and $R_2$ is at least 2, $R_3$ is hydrogen or an unsubstituted or substituted alkyl group, X is alkylene, oxaalkylene or thiaalkylene, and V is a radical of the formula

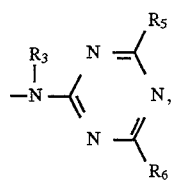

wherein $R_5$ and $R_6$ are each independently of the other hydrogen, halogen, lower alkyl, lower alkoxy, amino, mono-lower alkylamino, di-lower alkylamino, di(hydroxy lower alkyl)amino, morpholino phenoxy, phenylamino, phenylamino substituted by sulfo, phenyl-lower alkylamino and M is hydrogen an alkali metal, alkaline earth metal, ammonium or organic ammonium radical.

2. A sterically hindered phenol according to claim 1, wherein X is straight-chain or branched $C_1$-$C_8$alkylene.

3. A sterically hindered phenol according to claim 1, wherein $R_3$ is hydrogen or straight-chain or branched $C_1$-$C_8$alkyl.

4. A sterically hindered phenol according to claim 1, wherein $R_3$ is hydrogen.

5. A sterically hindered phenol according to claim 1, wherein $R_1$ and $R_2$ are each independently of the other methyl or tert-butyl.

6. A compound according to claim 1, wherein one of $R_5$ and $R_6$ is di(hydroxyethyl)amino or morpholino and the other is phenylamino or phenylamino substituted by sulfo.

* * * * *